United States Patent [19]

Ravichandran

[11] Patent Number: 5,021,480

[45] Date of Patent: Jun. 4, 1991

[54] AZO FREE RADICAL INITIATORS CONTAINING HINDERED AMINE MOIETIES WITH LOW BASICITY

[75] Inventor: Ramanathan Ravichandran, Nanuet, N.Y.

[73] Assignee: Ciba-Geigy Corporation, Ardsley, N.Y.

[21] Appl. No.: 480,175

[22] Filed: Feb. 14, 1990

Related U.S. Application Data

[63] Continuation-in-part of Ser. No. 326,850, Mar. 21, 1989, abandoned.

[51] Int. Cl.$^5$ .................. C08K 5/3435; C07D 211/34; C07D 211/40; C07D 211/58
[52] U.S. Cl. ..................................... 524/99; 524/102; 524/103; 546/16; 546/188; 546/190; 546/204; 546/206; 546/229; 546/230; 546/242; 546/246; 546/247
[58] Field of Search .................. 524/99, 102, 103; 546/16, 188, 190, 204, 206, 229, 230, 242, 246, 247

[56] References Cited

U.S. PATENT DOCUMENTS

3,994,857 11/1976 Holt ...................................... 524/103
4,665,185 5/1987 Winter et al. ........................ 546/192

OTHER PUBLICATIONS

Shlyapintokh et al., "Developments in Polymer Stabilisation", V, 41–70, (1982).
Chemical Abstracts, vol. 79, 105051b, 1973.

*Primary Examiner*—Kriellion Morgan
*Attorney, Agent, or Firm*—Luther A. R. Hall

[57] ABSTRACT

Compounds which contain azo linkages as well as a hindered amine light stabilizer moiety of low basicity function as free radical polymerization initiators and provide a polymer containing a hindered amine stabilizer chemically bonded to said polymer. The low basicity of the instant compounds prevents interaction with acid catalysts used in some polymerization systems.

27 Claims, No Drawings

AZO FREE RADICAL INITIATORS CONTAINING HINDERED AMINE MOIETIES WITH LOW BASICITY

This is a continuation-in-part of application Ser. No. 326,850, filed on Mar. 21, 1989, now abandoned.

The instant invention pertains to hindered amine light stabilizers which combine low basicity with an azo group in the same molecule.

Copending application Ser. No. 326,353 describes peroxide initiators containing hindered amine moieties with low basicity in the same molecule.

BACKGROUND OF THE INVENTION

The initiation of the polymerization of acrylic monomers with peroxy esters bearing hindered amine light stabilizing substituents is described by P. A. Callais et al in a paper presented in February 1988 at the "Waterborne and Higher Solids Coating Symposium" in New Orleans and published in Modern Paint and Coatings, 78 (9), 41 (1988).

Peroxides as free radical initiators containing hindered amine moieties is described in European Patent Application No. 233,476.

The combination of ultraviolet stabilizers (UV absorbers) with free radical initiating moieties (azo derivatives and peroxide compounds) are disclosed in U.S. Pat. Nos. 3,956,269; 4,042,773; 4,045,426; 4,045,427; 4,055,714 and 4,129,586.

4,4'-Azo-bis(4-cyano-2,2,6,6-tetramethylpiperin-4-yl) and 4,4'-azo-bis(4-cyano-1-oxyl-2,2,6,6-tetramethylpiperidin-4-yl) are disclosed as plastic additives in Chem. Abst. 79, 105051b.

The instant invention overcomes the drawbacks of the prior art materials which combine hindered amines with high basicity with peroxy groups.

The high basicity can neutralize acid catalysts that are commonly used in thermosetting resins thus causing cure inhibition. In other applications, the high basicity of many hindered amines can lead to undesired complexing and deactivation of metal ions which are used as catalysts for oxidative curing processes as well as undesired interactions with some pigment systems.

THE INVENTION

The thermal cleavage of the azo moiety in the molecule results in the formation of free radicals which can be used to initiate free radical polymerization of ethylenically unsaturated monomers.

Another application involves the grafting of the stabilizer to existing substrates including a variety of polymers.

In either of these two situations, the instant light stabilizing hindered amine moiety becomes substantially chemically bonded to the substrate and becomes concomitantly resistant to migration, exudation, leaching, sublimation, volatilization or any process which is prone to remove an additive physically from the substrate it is supposed to protect.

DETAILED DISCLOSURE

The instant invention pertains to a compound having in the same molecule a hindered amine moiety of low basicity and an azo free radical initiating moiety, said compound having the formula I

where
$E_1$ is a radical of the formula

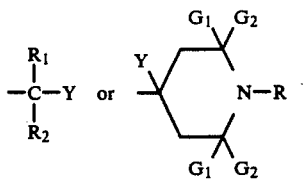

where $R_1$ and $R_2$ are independently alkyl of 1 to 36 carbon atoms, cycloalkyl of 5 to 12 carbon atoms, aralkyl of 7 to 20 carbon atoms, or $R_1$ and $R_2$ together are alkylene of 2 to 10 carbon atoms, or one of $R_1$ and $R_2$ is a group of formula II

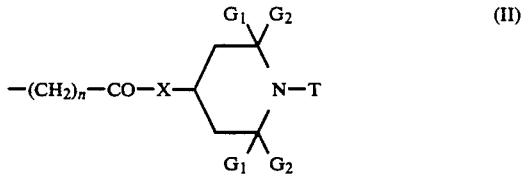

Y is —CN, —N$_3$, —COOT$_1$, —CONH$_2$, —OT$_1$, —ST$_1$, —OOH or —OH, $G_1$ and $G_2$ are independently alkyl of 1 to 4 carbon atoms, or $G_1$ and $G_2$ together are pentamethylene, X is —O—, —NH—, —NT$_1$— or

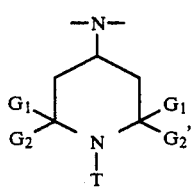

T is formyl, —OT$_1$ or —OCOT$_2$,
where
$T_1$ is alkyl of 1 to 36 carbon atoms, cycloalkyl of 5 to 12 carbon atoms, alkenyl of 3 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl, $T_2$ is alkyl of 1 to 18 carbon atoms, alkoxy of 1 to 18 carbon atoms, phenyl or said phenyl substituted by hydroxy, alkyl or alkoxy; or amino or said amino mono- or disubstituted by alkyl or phenyl, and $E_2$ has the same meaning as $E_1$ or $E_2$ is alkyl of 1 to 36 carbon atoms, cycloalkyl of 5 to 12 carbon atoms or aralkyl of 7 to 20 carbon atoms, with the proviso that one of $E_1$ or $E_2$ must contain a group having a

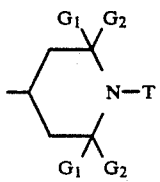

moiety present.

Preferably E₁ and E₂ are the same.

G₁ and G₂ are preferably each methyl.

R₁ and R₂ are preferably each alkyl of 1 to 4 carbon atoms, most preferably methyl.

R₁ is preferably a group of formula II where n is 2.

Y is preferably —CN.

X is preferably —O—, —NH— or

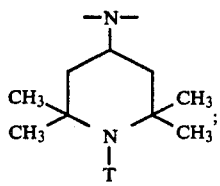

most preferably —O— or —NH—.

T is preferably formyl or —OT₁, where T₁ is alkyl of 1 to 18 carbon atoms, alkenyl of 2 to 3 carbon atoms, propargyl, alpha-methylbenzyl or cyclohexyl.

Most preferably T₁ is methyl, heptyl, octyl, nonyl or cyclohexyl.

Preferably T₂ is alkyl of 1 to 18 carbon atoms; most preferably alkyl of 1 to 12 carbon atoms.

The instant invention also pertains to a process of preparing a homo- or copolymer containing a hindered amine light stabilizer moiety chemically bonded to the backbone of said polymer which process comprises polymerizing one or more ethylenically unsaturated monomer capable of being polymerized by free radicals in the presence of an effective initiating amount of a compound of formula I.

The instant invention also relates to the stabilized polymer prepared by the process described above.

The instant invention also relates to compositions stabilized against the deleterious effects of actinic light which compositions contain a stabilized polymer made by the process described supra.

The instant invention also pertains to compositions stabilized against the deleterious effects of actinic light which comprise (a) a polymer, and (b) an effective stabilizing amount of a compound of formula I.

The instant compounds can be prepared by methods known in the art.

The intermediates used to make the instant compounds are generally items of commerce.

DETAILED DESCRIPTION OF THE INVENTION

Unsaturated polyester resins that can be cured by the compound of this invention usually include an unsaturated polyester and one or more polymerizable monomers. The unsaturated polyesters are, for instance, obtained by esterifying at least one ethylenically unsaturated di-or polycarboxylic acid, anhydride, or acid halide, such as maleic acid, fumaric acid, glutaconic acid, itaconic acid, mesaconic acid, citraconic acid, allylmalonic acid, allylsuccinic acid, tetrahydrophthalic acid and others with saturated or unsaturated di-or polyols, such as ethylene glycol, diethylene glycol, triethylene glycol, 1,2-and 1,3-propanediols, 1,2-, 1,3-and, 1,4-butanediols, 2,2-dimethyl-1,3-propanediols, 2,2-dimethyl-1,3-propanediol, 2-hydroxymethyl-2-methyl-1,3-propanediol, 2-buten-1,4-diol, 2,2,4-trimethyl-1,3-pentanediol, glycerol, pentaerythritol, mannitol and others. Mixtures of such polyacids and/or mixtures of such polyalcohols may also be used. The unsaturated di-or polycarboxylic acids may be partially replaced by saturated polycarboxylic acids, such as adipic acid, succinic acid, sebacic acid, and others and/or by aromatic polycarboxylic acids, such as phthalic acid, trimellitic acid, pyromellitic acid, isophthalic acid, and terephthalic acid. The acids used may be substituted by groups such as halogen. Examples of such suitable halogenated acids are, for instance, tetrachlorophthalic acid, 5,6-dicarboxy-1,2,3,4,7,7-hexachlorobicyclo[2.2.1]heptane, and others.

The other component of the unsaturated polyester resin, the polymerizable monomer or monomers, are preferably ethylenically unsaturated monomers, such as styrene, chlorostyrene, vinyltoluene, divinylbenzene, alpha-methylstyrene, diallyl maleate, diallyl phthalate, dibutyl fumarate, acrylonitrile, triallyl phosphate, triallyl cyanurate, methyl acrylate, methyl methacrylate, n-butyl methacrylate, ethyl acrylate, 2-hydroxyethyl methacrylate and others or mixtures thereof, which are copolymerizable with said polyesters.

A preferred unsaturated polyester resin contains as the polyester component the esterificaton product of 1,2-propylene glycon (a polyalcohol), maleic anhydride (an anhydride of an unsaturated polycarboxylic acid) and phthalic anhydride (an anhydride of an aromatic dicarboxylic acid) as well as the monomer component, styrene.

Other unsaturated polyester resins that are useful in the practice of this invention are unsaturated vinyl ester resins, consisting of a vinyl ester resin component and one or more polymerizable monomer components. The vinyl ester resin component can be made by reacting a chloroepoxide such as epichlorohydrin with appropriate amounts of a glycol such as bisphenol A (2,2-di-(4-hydroxyphenyl)-propane, in the presence of a base such as sodium hydroxide, to yield a condensation product having terminal epoxy groups derived from the epichlorohydrin. Subsequent reaction of the condensation product with polymerizable unsaturated carboxylic acids in the presence or absence of acidic or basic catalysts, results in the formation of a vinyl ester terminated resin component. Normally, styrene is added as the polymerizable monomer component to complete the preparation of the unsaturated vinyl ester resin.

Temperatures of about 20° to 200° C. and azo initiator levels of about 0.05 to 5% or more by weight of curable unsaturated polyester resin are normally employed in the curing process. The unsaturated polyester resins described above can be filled with various materials such as sulfur, glass fibers, carbon blacks, silicas, metal silicates, clays, metal carbonates, antioxidants, heat and light stabilizers, sensitizers, dyes, pigments, accelerators, metal oxides such as zinc oxide, blowing agents, etc.

The hindered amine-azo compound of the present invention is useful as a free radical initiator system for the polymerization or copolymerization of an ethylenically unsaturated monomer or mixtures thereof at suitable temperatures and pressures. The compound is useful not only in conventional isothermal polymerization processes but also in processes in which two or more increasing temperature steps are employed or a continuous increase in temperature is employed. Ethylenically unsaturated monomers include: olefins such as ethylene, propylene, styrene, alpha-methyl styrene, chlorostyrene, vinyl benzyl chloride, vinyl toluene, vinyl pyridine, divinyl benzene; diolefins such as 1,3-butadiene, isoprene and chloroprene; vinyl esters such as vinyl acetate, vinyl propionate, vinyl laurate, vinyl benzoate or divinyl carbonate; unsaturated nitriles such as acrylonitrile and methacrylonitrile; acrylic acid, methacrylic acid and their esters and amides, such as methyl, ethyl, n-butyl and 2-ethylhexyl acrylates and methacrylates and acrylamide and methacrylamide; maleic anhydride; maleimide and N-substituted derivatives thereof such as n-phenylmaleimide; maleic and fumaric acids and their esters; vinyl halo and vinylidene halo compounds such as vinyl chloride, vinyl fluoride, vinylidene chloride and vinylidene fluoride; perhalo olefins such as tetrafluoroethylene, hexafluoropropylene and chlorotrifluoroethylene; vinyl esters such as methyl vinyl ether, ethyl vinyl ether, n-butyl vinyl ether; allyl esters such as allyl acetate, allyl benzoate, diallyl phthalate, allyl ethyl carbonate, triallyl phosphate, triallyl cyanurate, diallyl fumarate, diallyl succinate, and diallyl carbonate; acrolein; methyl vinyl ketone; and mixtures thereof.

Temperatures of 30° to 250° C., preferably 40° to 200° C., and azo initiator levels of 0.005 to 3%, preferably 0.01 to 1%, by weight, based on monomer, are normally employed in the conventional polymerization or in the increasing temperature polymerization processes. Polymerization can be carried out in solution where solvents such as toluene may be used. Bulk, solution, suspension, or emulsion polymerization processes may be employed. The hindered amine-azo initiator compound of this invention may be employed in these vinyl polymerization processes alone or together with other peroxides and azo initiators.

The hindered amine-azo initiator compound of this invention is also useful for producing high impact polymers such as high impact polystyrene by initiating grafting of a monomer onto the backbone of elastomers (rubbers) such as polybutadienes, styrene-butadiene-styrene triblock copolymers, ethylene-propylene-diene terpolymers, etc. This composition is also useful with lower amounts of the rubber to produce high impact resistant polymers having impact resistance comparable to high impact polymers produced with larger amounts of rubber and conventional initiator systems. The above described vinyl polymerization conditions and initiator levels and up to 15% by weight of rubber (based on monomer) may be used for producing high impact polymers.

The ethylenically unsaturated comonomers may also contain a UV-absorbing moiety such as a hydroxyphenyl substituted benzotriazole or s-triazine, a hydroxy substituted benzophenone, an oxanilide or alpha-cyanocinnamate or a hindered amine light stabilizing moiety. Examples of such ethylenically unsaturated UV-absorbers are described in a number of United States patents which are hereby incorporated into this application by reference.

Ethylenically unsaturated UV absorbers are described in a number of U.S. Patents. Acrylated benzotriazoles are described in U.S. Pat. Nos. 4,413,095; 4,716,234; 4,785,063 and 4,803,254. Acryloxyalkyl benzotriazoles are described in U.S. Pat. No. 4,260,768. Vinyl substituted benzotriazoles are described in U.S. Pat. No. 4,508,882. Ethylenically unsaturated benzotriazoles are described in U.S. Pat. No. 3,493,539. Acrylated benzophenones are described in U.S. Pat. No. 4,310,650.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

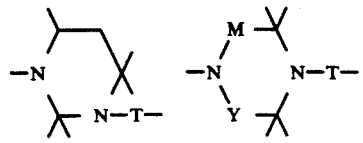

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA-or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl-butyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as blockcopolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or silicone-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants
   1.1. Alkylated monophenols, for example,
   2,6-di-tert-butyl-4-methylphenol
   2-tert-butyl-4,6-dimethylphenol
   2,6-di-tert-butyl-4-ethylphenol
   2,6-di-tert-butyl-4-n-butylphenol
   2,6-di-tert-butyl-4-i-butylphenol
   2,6-di-cyclopentyl-4-methylphenol
   2-(α-methylcyclohexyl)-4,6-dimethylphenol
   2,6-di-octadecyl-4-methylphenol
   2,4,6-tri-cyclohexylphenol
   2,6-di-tert-butyl-4-methoxymethylphenol
   1.2. Alkylated hydroquinones, for example,
   2,6-di-tert-butyl-4-methoxyphenol
   2,5-di-tert-butyl-hydroquinone
   2,5-di-tert-amyl-hydroquinone
   2,6-diphenyl-4-octadecyloxyphenol
   1.3. Hydroxylated thiodiphenyl ethers, for example
   2,2'-thio-bis-(6-tert-butyl-4-methylphenol)
   2,2'-thio-bis-(4-octylphenol)
   4,4'-thio-bis-(6-tert-butyl-3-methylphenol)
   4,4'-thio-bis-(6-tert-butyl-2-methylphenol)
   1.4. Alkylidene-bisphenols, for example,
   2,2'-methylene-bis-(6-tert-butyl-4-methylphenol)
   2,2'-methylene-bis-(6-tert-butyl-4-ethylphenol)
   2,2'-methylene-bis-[4-methyl-6-(α-methylcyclohexyl)-phenol]
   2,2'-methylene-bis-(4-methyl-6-cyclohexylphenol)
   2,2'-methylene-bis-(6-nonyl-4-methylphenol)
   2,2'-methylene-bis-[6-(α-methylbenzyl)-4-nonylphenol]
   2,2'-methylene-bis-[6-(α,α-dimethylbenzyl)-4-nonylphenol]
   2,2'-methylene-bis-(4,6-di-tert-butylphenol)
   2,2'-ethylidene-bis-(4,6-di-tert-butylphenol)
   2,2'-ethylidene-bis-(6-tert-butyl-4-isobutylphenol)
   4,4'-methylene-bis-(2,6-di-tert-butylphenol)
   4,4'-methylene-bis-(6-tert-butyl-2-methylphenol)
   1,1-bis-(5-tert-butyl-4-hydroxy-2-methylphenyl-butane
   2,6-di-(3-tert-butyl-5-methyl-2-hydroxybenzyl)-4-methylphenol
   1,1,3-tris-(5-tert-butyl-4-hydroxy-2-methylphenyl)-butane
   1,1-bis-(5-tert-butyl-4-hydroxy-2-methylphenyl)-3-n-dodecylmercaptobutane
   ethyleneglycol bis-[3,3-bis-(3'-tert-butyl-4'-hydroxyphenyl)-butyrate]
   di-(3-tert-butyl-4-hydroxy-5-methylphenyl)-dicyclopentadiene
   di-[2-(3'-tert-butyl-2'-hydroxy-5'-methyl-benzyl)-6-tert-butyl-4-methylphenyl] terephthalate.
   1.5. Benzyl compounds, for example,
   1,3,5-tri-(3,5-di-tert-butyl-4-hydroxybenzyl)-2,4,6-trimethylbenzene
   di-(3,5-di-tert-butyl-4-hydroxybenzyl) sulfide
   3,5-di-tert-butyl-4-hydroxybenzyl-mercapto-acetic acid isooctyl ester
   bis-(4-tert-butyl-3-hydroxy-2,6-dimethylbenzyl)dithiol terephthalate
   1,3,5-tris-(3,5-di-tert-butyl-4-hydroxybenzyl) isocyanurate
   1,3,5-tris-(4-tert-butyl-3-hydroxy-2,6-dimethylbenzyl) isocyanurate
   3,5-di-tert-butyl-4-hydroxybenzyl-phosphoric acid di-octadecyl ester
   3,5-di-tert-butyl-4-hydroxybenzyl-phosphoric acid monoethyl ester, calcium-salt
   1.6. Acylaminophenols, for example,
   4-hydroxy-lauric acid anilide
   4-hydroxy-stearic acid anilide
   2,4-bis-octylmercapto-6-(3,5-tert-butyl-4-hydroxyanilino)s-triazine
   octyl-N-(3,5-di-tert-butyl-4-hydroxyphenyl)-carbamate
   1.7. Esters of β-(3,5-di-tert-butyl-4-hydroxyphenyl)-propionic acid with monohydric or polyhydric alcohols, for example,
   methanol
   octadecanol
   1,6-hexanediol
   neopentyl glycol
   thiodiethylene glycol
   diethylene glycol
   triethylene glycol
   pentaerythritol
   tris-hydroxyethyl isocyanurate
   di-hydroxyethyl oxalic acid diamide
   1.8. Esters of β-(5-tert-butyl-4-hydroxy-3-methylphenyl)propionic acid with monohydric or polyhydric alcohols, for example,
   methanol
   octadecanol
   1,6-hexanediol
   neopentyl glycol
   thiodiethylene glycol
   diethylene glycol
   triethylene glycol
   pentaerythritol
   tris-hydroxyethyl isocyanurate
   di-hydroxyethyl oxalic acid diamide
   1.9. Amides of β-(3,5-di-tert-butyl-4-hydroxyphenyl)-propionic acid for example,
   N,N'-di-(3,5-di-tert-butyl-4-hydroxyphenylpropionyl)-hexamethylenediamine
   N,N'-di-(3,5-di-tert-butyl-4-hydroxyphenylpropionyl)-trimethylenediamine
   N,N'-di-(3,5-di-tert-butyl-4-hydroxyphenylpropionyl)-hydrazine
2. UV absorbers and light stabilizers
   2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.
   2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.
   2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.
   2.4. Acrylates, for example, α-cyano-β,β-diphenylacrylic acid ethyl ester or isooctyl ester, α-carbomethoxy-cinnamic acid methyl ester, α-cyano-β-methyl-p- methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o-and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy-4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine; 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite.

11. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1 Par 2, on pages 735 and 742 (Berlin 1972), "Lackkunstharze" (1977), by H. Wagner and H. F. Sarx, on pages 229-238, and in S. Paul's "Surface Coatings: Science and Technology" (1985).

The polyester lacquers, which can be stabilized against the action of light and moisture, are the conventional stoving lacquers described e.g. in H. Wagner and H. F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/melamine resins and alkyd/acrylic/melamine resins (see H. Wagner and H. F. Sarx, op. cit., pages 99-123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with the aforementioned piperidine compounds are references in a paper by H. J. Heller in European Polymer Journal Supplement, 1969, pp. 105–132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, and 3',5'-di-tert-amyl derivatives.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

(c) Acrylates, for example, alpha-cyano-$\beta,\beta$-diphenylacrylic acid ethyl ester or isoctyl ester, alpha-carbomethoxy-cinnamic acid methyl ester, alpha-cyano-$\beta$-methyl-p-methoxy-cinnamic acid methyl ester or butyl ester, alpha-carbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyloxanilide and its mixture with 2-ethoxy-2'-ethyl-5,4'-di-tert-butyl-oxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di (alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octylphenyl)-2H-benzotriazole, 2-(2-hydroxy-3-tert-octyl-5-alpha,alpha-dimethylbenzylphenyl)-2H-benzotriazole, 2-(2-hydroxy-3,5-di-tert-amylphenyl)-2H-benzotriazole, 2-[2-hydroxy-3-tert-butyl-5-(2-(omega-hydroxy-octa-(ethyleneoxy)carbonyl)-ethylphenyl]-2H-benzotriazole, dodecylated 2-(2-hydroxy-5-methylphenyl)-2H-benzotriazole, 2-[2-hydroxy-3-tert-butyl-5-(2-octyloxycarbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alpha-dimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert-butyl-5-(2-octyloxycarbonyl)ethylphenyl]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising (a) an acid catalyzed thermoset coating or enamel based on hot crosslinkable acrylic, polyester or alkyd resins, (b) a $NOT_1$-substituted 2,2,6,6-tetralkylpiperidine compound, and (c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, di-isodecylpentaerythritol diphosphite, di-(2,4-di-tert.butylphenyl)pentaerythritol diphosphite, tristearylsorbitol triphosphite, tetrakis-(2,4-di-tert.butylphenyl)-4,4'-di-phenylylenediphosphonite.

The acid catalyzed theremoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

Still another preferred combination of the instant stabilizers is with the hydroxylamine in order to protect polypropylene fibers from gas fading.

The following examples are presented for the purpose of illustration only and are not to be construed to limit the nature or scope of the instant invention in any manner whatsoever.

EXAMPLE 1

Di-(1-methoxy-2,2,6,6-tetramethylpiperidin-4-yl) 4,4'-azobis(4-cyanovalerate)

To a stirred suspension of 4,4'-azobis(4-cyanovaleric acid) (2.8 grams) in 20 ml of tetrahydrofuran is added 2.1 ml of oxalyl chloride. After stirring at room temperature for three hours, the solvent and excess oxalyl chloride are removed under reduced pressure. The acid chloride formed is dissolved in toluene and then added to a stirred solution of 1-methoxy-4-hydroxy-2,2,6,6-tetramethylpiperidine (3.51 grams) and 2.0 ml of pyridine in 20 ml of methylene chloride at 0° C. After stirring at room temperature for one hour, the reaction mixture is concentrated and the residue is purified by liquid chromatography to afford the title compound as a mixture of cis and trans isomers.

Analysis: Calcd for $C_{32}H_{54}N_6O_6$: C, 62.1; H, 8.8; N, 13.6. Found: C, 61.8; H, 9.0; N, 13.3.

EXAMPLES 2–14

Using the general procedure of Example 1, the compounds of the following formula are prepared.

| Example | X | T |
|---------|-----|--------------|
| 2 | —O— | cyclohexyloxy |
| 3 | —NH— | cyclohexyloxy |
| 4 | —O— | octyloxy |
| 5 | —NH— | octyloxy |
| 6 | —O— | hydroxyl |
| 7 | —NH— | methoxy |
| 8 | —O— | methoxy |
| 9 | —O— | heptyloxy |
| 10 | —NH— | formyl |
| 11 | —NH— | heptyloxy |
| 12 | —NH— | methoxy |
| 13 | —N— (piperidine ring) | octyloxy |
| 14 | (T same as in column T) | cyclohexyloxy |

EXAMPLES 15-26

Using the general procedure of Example 1, the compounds of the following formula are prepared.

$$\text{T-N}\underset{CH_3\ CH_3}{\overset{CH_3\ CH_3}{\diagup\diagdown}}\text{-X-CO(CH}_2)_2\underset{CN}{\overset{CH_3}{\text{C}}}\text{-N=N-}\underset{CN}{\overset{CH_3}{\text{C}}}\text{(CH}_2)_2\text{CO-X-}\underset{CH_3\ CH_3}{\overset{CH_3\ CH_3}{\diagdown\diagup}}\text{N-T}$$

| Example | X | T |
|---|---|---|
| 15 | —O— | cyclohexyloxy |
| 16 | —NH— | nonyloxy |
| 17 | —NH— | heptyloxy |
| 18 | —O— | nonyloxy |
| 19 | —NH— | octyloxy |
| 20 | —O— | octadecyloxy |
| 21 | —O— | allyloxy |
| 22 | —O— | hydroxy |
| 23 | —O— | formyl |
| 24 | —O— | heptyloxy |
| 25 | (piperidinyl-N-T) | methoxy |

EXAMPLES 27-34

Following the general method described in U.S. Pat. No. 2,711,405, a 1-hydrocarbyloxy-2,2,6,6-tetramethyl-4-piperidone cyanohydrin is reacted with ammonia to yield the corresponding alpha-aminonitrile. Oxidation of the alpha-aminonitrile with sodium hypochlorite solution at temperatures below 10° C. affords the corresponding bis-azo compound of the structure below.

$$\text{T-N}\underset{CH_3\ CH_3}{\overset{CH_3\ CH_3}{\diagup\diagdown}}\underset{CN}{\overset{CN}{\text{-N=N-}}}\underset{CH_3\ CH_3}{\overset{CH_3\ CH_3}{\diagdown\diagup}}\text{N-T}$$

| Example | T |
|---|---|
| 27 | methoxy |
| 28 | cyclohexyloxy |
| 29 | octyloxy |
| 30 | octadecyloxy |
| 31 | allyloxy |
| 32 | hydroxy |
| 33 | formyl |
| 34 | nonyloxy |

EXAMPLE 35

Di-(1-octyloxy-2,2,6,6-tetramethylpiperidin-4-yl) 4,4'-azobis-(4-cyanovalerate)

To a solution of 4,4'-azobis(4-cyanovaleric acid) (0.77 gram) and 1.53 grams of 4-hydroxy-1-octyloxy-2,2,6,6-tetramethylpiperidine in 15 ml of tetrahydrofuran is added 1.16 grams of dicyclohexylcarbodiimide at room temperature. After stirring the reaction mixture overnight, an additional 0.3 gram of dicyclohexylcarbodiimide and 0.2 gram of dimethylaminopyridine are added and the reaction mixture is stirred at room temperature for an additional eight hours. The crude reaction mixture is quenched by the addition of 0.5 ml of acetic acid and the precipitated urea is removed by filtration. The filtrate is concentrated under reduced pressure and the residue is purified by silica gel flash column chromatography (30:1, hexane: acetone eluent) to afford 1.3 grams of the title compound as a clear oil.

Analysis: Calcd. for $C_{46}H_{82}N_6O_6$: C, 67.8; H, 10.2; N, 10.3. Found: C, 67.8; H, 10.4; N, 10.2.

EXAMPLE 36

N,N'-Di(1-cyclohexyloxy-2,2,6,6-tetramethylpiperidin-4-yl)4,4'-azobis(4-cyanovaleramide)

To a solution of 4,4'-azobis(4-cyanovaleric acid) (0.77 gram) and 1.44 grams of 4-amino-1-cyclohexyloxy-2,2,6,6-tetramethylpiperidine in 15 ml of acetonitrile is added 1.16 grams of dicyclohexylcarbodiimide. After stirring the reaction mixture for eight hours at room temperature, the reaction mixture is quenched with 0.5 ml of acetic acid and the precipitated urea is removed by filtration. The filtrate is purified by silica gel flash column chromatography to afford the title compound as a white solid.

EXAMPLE 37

Light Stabilization of Polypropylene

This examples illustrates the light stabilizing effectiveness of instant stabilizers.

Polypropylene powder (Himont Profax 6501) stabilized with 0.2% by weight of n-octadecyl 3,5-di-tert-butyl-4-hydroxyhydrocinnamate is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250° C. and 175 psi (1.2×10⁶ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive Compound of | Additive Concentration (% by weight) | FS/BL Test Results (hours to Failure) |
|---|---|---|
| Base Resin | — | 340 |
| Example 1 | 0.1 | 1700 |

The instant compounds are also effective stabilizers in poly(vinyl chloride) and ABS resin; and high solids thermoset acrylic coating resins prepared using these initiators exhibit outstanding durability and weatherability in both clear and basecoat/clearcoat applications.

EXAMPLE 38

A monomer composition comprising 25% butyl acrylate, 27% butyl methacrylate, 30% 2-hydroxyethyl acrylate, 15% styrene and 3% acrylic acid (all % values are by weight) and 16.4 g of the initiator prepared in Example 35 is polymerized in refluxing xylene to form a stabilized acrylic polyol polymer having N—OT₁ substituted hindered amine moieties chemically bonded to said polymer.

EXAMPLE 39

Stabilization of High Solids Thermoset Acrylic Resin Enamel

The stabilized acrylic polyol prepared in Example 38 is used to formulate a thermoset acrylic enamel.

The acrylic-melamine formulation comprises (all values are in parts by weight) 70 parts of acrylic polyol polymer as described above, 18 parts of melamine (Cymel 303, American Cyanamid, 0.51 part of sulfonic acid catalyst (Cycat 600, 70% DDBSA, American Cyanamid) 0.6 part of flow aid (FC 431 50% solids fluorocarbon, 3M) and 8.8 parts of methyl amyl ketone.

Commercially available epoxy primed 4"×12" (10.16 cm×30.48 cm) panels (Uniprime from Advanced Coatings Technology) are spray coated with a silver metallic basecoat to a thickness of about 0.8 mil (0.023 mm) and air dried for 3 minutes. The stabilized thermoset acrylic resin enamel is then sprayed onto the basecoated panel to a thickness of about 1.7 mil (0.049 mm). After 15 minutes air-drying, the coated sheets are baked for 30 minutes at 250° F. (121° C.).

After storage for 1 week in a air-conditioned room, the coated panels are subjected to weathering in a QUV exposure apparatus according to test method ASTM G-53/77. In this test, the samples are subjected to weathering in repeated cycles for 4 hours in a humid atmosphere at 50° C. and then for 8 hours under UV light at 70° C. The panels are exposed in the QUV for 1500 hours. The 20° gloss values of the panels are determined before and after exposure.

The loss of gloss of the stabilized panels is considerably less than that of the unstabilized control panels.

What is claimed is:

1. A compound having in the same molecule a hindered amine moiety of low basicity and an azo free radical initiating moiety, said compound having the formula I $$E_1-N=N-E_2 \quad (I)$$

where $E_1$ is a radical of the formula

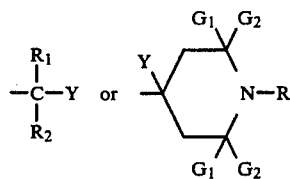

where $R_1$ and $R_2$ are independently alkyl of 1 to 36 carbon atoms, cycloalkyl of 5 to 12 carbon atoms, aralkyl of 7 to 20 carbon atoms, or $R_1$ and $R_2$ together are alkylene of 2 to 10 carbon atoms, or one of $R_1$ and $R_2$ is a group of formula II

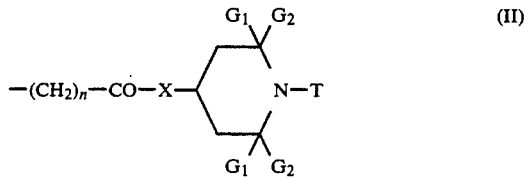

Y is —CN, —N₃, —COOT₁, —CONH₂, —OT₁, —ST₁, —OOH or —OH, $G_1$ and $G_2$ are independently alkyl of 1 to 4 carbon atoms, or $G_1$ and $G_2$ together are pentamethylene, X is —O—, —NH—, —NT₁— or

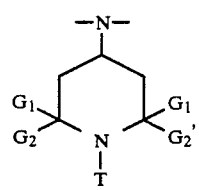

T is formyl, —OT₁ or —OCOT₂, where $T_1$ is alkyl of 1 to 36 carbon atoms, cycloalkyl of 5 to 12 carbon atoms, alkenyl of 3 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl, $T_2$ is alkyl of 1 to 18 carbon atoms, alkoxy of 1 to 18 carbon atoms, phenyl or said phenyl substituted by hydroxy, alkyl or alkoxy; or amino or said amino mono- or disubstituted by alkyl or phenyl, and $E_2$ has the same meaning as $E_1$ or $E_2$ is alkyl of 1 to 36 carbon atoms, cycloalkyl of 5 to 12 carbon atoms or aralkyl of 7 to 20 carbon atoms, with the proviso that one of $E_1$ or $E_2$ must contain a group having a

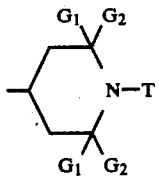

moiety present.

2. A compound according to claim 1 wherein $E_1$ and $E_2$ are the same.

3. A compound according to claim 1 wherein $G_1$ and $G_2$ are each methyl.

4. A compound according to claim 1 wherein $R_1$ and $R_2$ are each alkyl of 1 to 4 carbon atoms.

5. A compound according to claim 4 wherein $R_1$ and $R_2$ are each methyl.

6. A compound according to claim 1 wherein Y is —CN.

7. A compound according to claim 1 wherein X is —O—, —NH— or

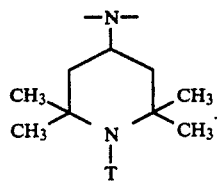

8. A compound according to claim 7 wherein X is —O— or —NH—.

9. A compound according to claim 1 wherein T is formyl or —$OT_1$, where $T_1$ is alkyl of 1 to 18 carbon atoms, alkenyl of 2 to 3 carbon atoms, propargyl, alpha-methylbenzyl or cyclohexyl.

10. A compound according to claim 9 wherein $T_1$ is methyl, heptyl, octyl, nonyl or cyclohexyl.

11. The compound according to claim 1 which is di-(1-methoxy-2,2,6,6-tetramethylpiperidin-4-yl) 4,4'-azobis(4-cyanovalerate).

12. The compound according to claim 1 which is di-(1-octyloxy-2,2,6,6-tetramethylpiperidin-4-yl) 4,4'-azobis(4-cyanovalerate).

13. The compound according to claim 1 which is N,N'-di-(1-cyclohexyloxy-2,2,6,6-tetramethylpiperidin-4-yl)-4,4'-azobis(4-cyanovaleramide).

14. A process of preparing a light-stable homo- or copolymer containing a hindered amine light stabilizer moiety chemically bonded to the backbone of said polymer which process comprises polymerizing one or more ethylenically unsaturated monomers capable of being polymerized by free radicals in the presence of an effective initiating amount of a compound of formula I according to claim 1.

15. A polymer stabilized against the deleterious effects of actinic light which is produced by the process according to claim 14.

16. A composition stabilized against the deleterious effects of actinic light which composition contains a stabilized polymer made by the process according to claim 14.

17. A composition stabilized against the deleterious effects of actinic light which comprises
   (a) a polymer, and
   (b) an effective stabilizing amount of a compound according to claim 1.

18. A composition according to claim 17 wherein the polymer is a polyolefin.

19. A composition according to claim 18 wherein the polyolefin is polypropylene.

20. A composition according to claim 17 wherein the polymer is a coating system based on alkyd, acrylic, acrylic-alkyd, polyester, epoxide, urethane, polyamide, vinyl or epoxy-polyester resins.

21. A composition according to claim 17 wherein component (b) is di-(1-methoxy-2,2,6,6-tetramethylpiperidin-4-yl) 4,4'-azobis(4-cyanovalerate).

22. A composition according to claim 17 wherein component (b) is di-(1-octyloxy-2,2,6,6-tetramethylpiperidin-4-yl) 4,4'-azobis(4-cyanovalerate).

23. A composition according to claim 20 which contains a UV absorber or additional light stabilizer.

24. A composition according to claim 17 wherein the polymer is an unsaturated elastomer which is polybutadiene, polyisoprene, styrene-butadiene copolymer or block copolymer, ethylene-propylene terpolymer, isoprene-isobutylene copolymer, acrylonitrile-butadiene copolymer, or styrene-isoprene copolymer or block copolymer.

25. A composition according to claim 24 wherein the elastomer is styrene-butadiene copolymer or block copolymer, styrene-isoprene copolymer or block copolymer or polybutadiene.

26. A composition according to claim 17 wherein component (a) is unsaturated and component (b) is grafted to component (a).

27. A method for stabilizing an synthetic polymer against oxidative, thermal or actinic degradation which comprises incorporating into said synthetic polymer an effective stabilizing amount of a compound according to claim 1.

* * * * *